(12) United States Patent
Schauf

(10) Patent No.: US 10,610,198 B2
(45) Date of Patent: Apr. 7, 2020

(54) AUTOMATED SWEEP AND EXPORT OF 2D ULTRASOUND IMAGES OF 3D VOLUMES

(75) Inventor: Michael Schauf, Bothell, WA (US)

(73) Assignee: Koninklijke Philips N.V., Eindhoven (NL)

( * ) Notice: Subject to any disclaimer, the term of this patent is extended or adjusted under 35 U.S.C. 154(b) by 1285 days.

(21) Appl. No.: 13/812,557

(22) PCT Filed: Jul. 20, 2011

(86) PCT No.: PCT/IB2011/053225
§ 371 (c)(1),
(2), (4) Date: Apr. 9, 2013

(87) PCT Pub. No.: WO2012/014125
PCT Pub. Date: Feb. 2, 2012

(65) Prior Publication Data
US 2013/0194890 A1      Aug. 1, 2013

Related U.S. Application Data

(60) Provisional application No. 61/369,195, filed on Jul. 30, 2010.

(51) Int. Cl.
*A61B 8/00* (2006.01)
*A61B 8/14* (2006.01)
(Continued)

(52) U.S. Cl.
CPC .............. *A61B 8/145* (2013.01); *A61B 8/463* (2013.01); *A61B 8/543* (2013.01); *G01S 7/52063* (2013.01); *G01S 7/52074* (2013.01); *G01S 7/52087* (2013.01); *G01S 15/8906* (2013.01); *G01S 15/8993* (2013.01);
(Continued)

(58) Field of Classification Search
USPC ............................................................. 367/7
See application file for complete search history.

(56) References Cited

U.S. PATENT DOCUMENTS 4,528,854 A * 7/1985 Shimazaki ........... G01N 29/262
367/105
5,722,412 A * 3/1998 Pflugrath ................. A61B 8/00
600/441
(Continued)

FOREIGN PATENT DOCUMENTS

| JP | 08107895 A | 4/1996 |
|---|---|---|
| JP | 2005185333 A | 7/2005 |

(Continued)

OTHER PUBLICATIONS

International Preliminary Report on Patentability for PCT/IB2011/053225, dated Feb. 25, 2013. 8 pages.*

*Primary Examiner* — James R Hulka

(57) ABSTRACT

An ultrasound system (10) which is capable of biplane imaging is able to display, store and export independent image frames of only the reference image or only the variable orientation image, or the standard display of both images. The system is also able to sweep through a range of image plane orientations and to automatically acquire an image in each orientation over the range of plane orientations. The system is preferably operable in the biplane tilt mode, the biplane rotate mode, or the biplane elevation tilt mode.

16 Claims, 5 Drawing Sheets

(51) Int. Cl.
*G01S 15/89* (2006.01)
*G01S 7/52* (2006.01)
*A61B 8/08* (2006.01)

(52) U.S. Cl.
CPC .............. *A61B 8/466* (2013.01); *A61B 8/483* (2013.01); *G01S 7/52073* (2013.01); *G01S 15/8925* (2013.01)

(56) References Cited

U.S. PATENT DOCUMENTS

| | | | |
|---|---|---|---|
| 5,997,479 A | 12/1999 | Savord et al. | |
| 6,213,944 B1* | 4/2001 | Miller | G01S 7/52087 386/E9.013 |
| 6,231,508 B1* | 5/2001 | Miller | G01S 7/52087 382/305 |
| 6,245,017 B1 | 6/2001 | Hashimoto et al. | |
| 6,277,075 B1* | 8/2001 | Torp | G01S 7/52039 600/443 |
| 6,436,048 B1 | 8/2002 | Pesque | |
| 6,582,367 B1* | 6/2003 | Robinson | A61B 8/14 600/443 |
| 6,669,641 B2 | 12/2003 | Poland | |
| 6,709,394 B2 | 3/2004 | Frisa | |
| 6,755,786 B2 | 6/2004 | Frisa et al. | |
| 6,875,177 B2* | 4/2005 | Mochizuki | A61B 8/4209 128/916 |
| 7,217,243 B2* | 5/2007 | Takeuchi | G01S 7/52046 600/447 |
| 7,347,820 B2* | 3/2008 | Bonnefous | A61B 8/483 600/437 |
| 7,604,595 B2* | 10/2009 | Steen | A61B 8/14 367/153 |
| 8,172,753 B2* | 5/2012 | Halmann | A61B 8/00 128/916 |
| 8,551,000 B2* | 10/2013 | Chiang | A61B 8/4483 600/437 |
| 8,852,103 B2* | 10/2014 | Rothberg | A61B 8/4254 600/438 |
| 9,022,936 B2* | 5/2015 | Rothberg | A61B 8/4254 600/438 |
| 9,028,412 B2* | 5/2015 | Rothberg | A61B 8/4254 600/438 |
| 9,033,884 B2* | 5/2015 | Rothberg | A61B 8/4254 600/438 |
| 9,044,196 B2* | 6/2015 | Schauf | A61B 8/02 |
| 2003/0032882 A1* | 2/2003 | Mochizuki | A61B 8/4209 600/443 |
| 2004/0267135 A1* | 12/2004 | Takeuchi | G01S 7/52046 600/459 |
| 2005/0281444 A1 | 12/2005 | Lundberg | |
| 2005/0283078 A1 | 12/2005 | Steen | |
| 2005/0283079 A1* | 12/2005 | Steen | A61B 8/14 600/447 |
| 2006/0074309 A1* | 4/2006 | Bonnefous | A61B 8/483 600/437 |
| 2009/0069679 A1 | 3/2009 | Hibi | |
| 2013/0085393 A1* | 4/2013 | Schauf | A61B 8/02 600/447 |
| 2013/0116561 A1* | 5/2013 | Rothberg | A61B 8/4254 600/438 |
| 2014/0180093 A1* | 6/2014 | Rothberg | A61B 8/4254 600/438 |
| 2014/0180099 A1* | 6/2014 | Rothberg | A61B 8/4254 600/439 |
| 2014/0180112 A1* | 6/2014 | Rothberg | A61B 8/4254 600/447 |

FOREIGN PATENT DOCUMENTS

| | | |
|---|---|---|
| JP | 2007038016 A | 2/2007 |
| JP | 2009153600 A | 7/2009 |
| WO | 0054518 A1 | 9/2000 |
| WO | 2009044316 A1 | 4/2009 |

* cited by examiner

AUTOMATED SWEEP AND EXPORT OF 2D ULTRASOUND IMAGES OF 3D VOLUMES

This invention relates to ultrasonic diagnostic systems and, in particular, to 3D ultrasonic diagnostic imaging systems which automatically sweep 2D image planes in relation to a reference plane and export swept planes as individual image planes or image sequences.

U.S. Pat. No. 6,709,394 (Frisa et al.) and U.S. Pat. No. 6,755,786 (Frisa et al.) describe ultrasonic biplane imaging. In biplane imaging a two-dimensional matrix array transducer probe scans two different 2D image planes in rapid alternating succession, thereby producing live real-time images of both planes. One of the image planes is denominated as the reference image plane. This image plane is generally oriented perpendicular to the plane of the matrix array transducer, extending straight out from the probe around a center orthogonal axis to the array. The reference image orientation is usually maintained stationary and the second image plane is movable in relation to this reference plane. The '394 patent describes biplane imaging in which the second image plane can be tilted or rotated with respect to the reference plane. In a commercial embodiment available from Philips Healthcare of Andover, Mass., the tilted image plane has a nominal orientation with its center axis in alignment with the center axis of the reference plane. The tilt plane can be moved (tilted) so that it is oriented at different angles in relation to the center axis of the reference plane but with its center axis always located in the reference plane. The rotational biplane implementation again has the center axis of the second (rotating) image plane aligned at the start with the center axis of the reference image and the second image orientation is orthogonal to the plane of the reference image. From this starting position the rotating plane can be rotated about its center axis at angles with respect to the reference image which vary from orthogonal. The '786 patent describes what is known as elevation tilt biplane imaging. In elevation tilt imaging the second image has a starting position in alignment with the reference image. The second image is then moved away from the reference image plane in the elevation dimension, to different planes which do not intersect the reference image plane. The two planes can thus be perfectly parallel or angularly parallel, the latter being a condition where the second plane has a common apex location with the reference plane or intersects the reference plane above the top (shallowest depth) of the images. Biplane images allow a clinician to position the reference plane to view a target anatomy or region of interest, then move the second plane to observe other planar images of the target anatomy. As shown in the patents, the two biplane images are displayed side-by-side at the same time, so that the clinician can constantly view the reference image while moving the second plane. Biplane imaging allows the clinician to scan and observe two image planes at the same time, while constantly maintaining his or her navigational bearings of the image locations within the three dimensional volume being scanned. When the clinician locates anatomy of interest in both image planes, a single image or a loop (sequence of live images) can be captured or save and displayed or replayed later when making a definitive diagnosis.

The capture of the dual display of images will reduce the size of each image compared to the size of the display of a single image. In some cases it may be desirable to save only the second image which has been located to observe anatomy requiring diagnosis; the reference image may not be necessary for the diagnosis. Saving only the second image would enable the image to be displayed in a larger display format which aids a detailed diagnosis. It may also be desirable to save, not just a single movable image, but all images over a range of image orientations. Manually repositioning the movable image to a series of new orientations, then capturing the new images in succession, is tedious and time-consuming and presents an incomplete series of images if the probe inadvertently moves during the process. It would be further desirable to be able to automatically step or sweep through a range of image orientations and capture all images in the range or sweep. It is further desirable to be able to save only the sequence of swept second images, independent of the reference image when the reference image is no longer useful to the diagnosis.

In accordance with the principles of the present invention, a diagnostic ultrasound imaging system performs biplane imaging with the capability of sweeping through and saving the images from a series of movable biplane image orientations. At the touch of a button the second (movable) plane of the biplane images is rotated, tilted, or elevated through the full range of orientations or a selected sub-range, and the sequence saved for later observation. In accordance with a further aspect of the present invention, the movable image plane or sequence of such planes, either static or live images, can be captured and saved separately from the reference plane image. An individual image or loop of images can then be exported for later viewing and diagnosis.

Figure 5B:
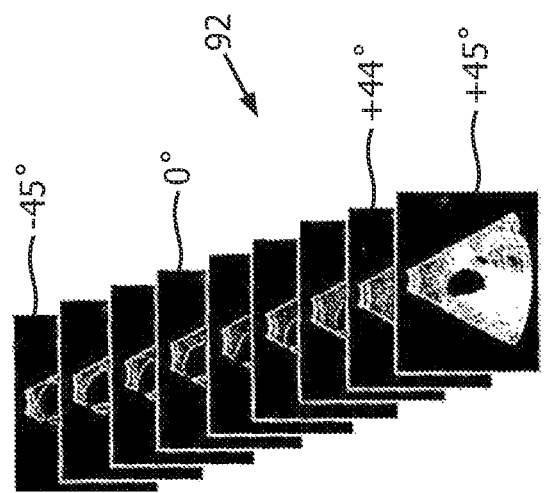
Figure 5A:
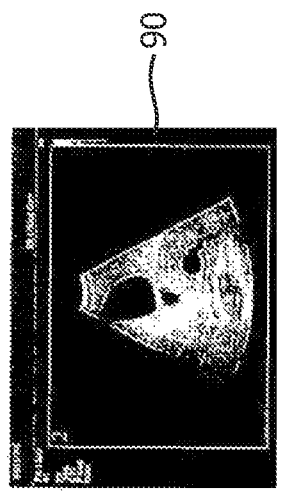

FIGS. 5*a* and 5*b* illustrate individually saved second (movable) biplane images in accordance with the principles of the present invention.

Figure 1:
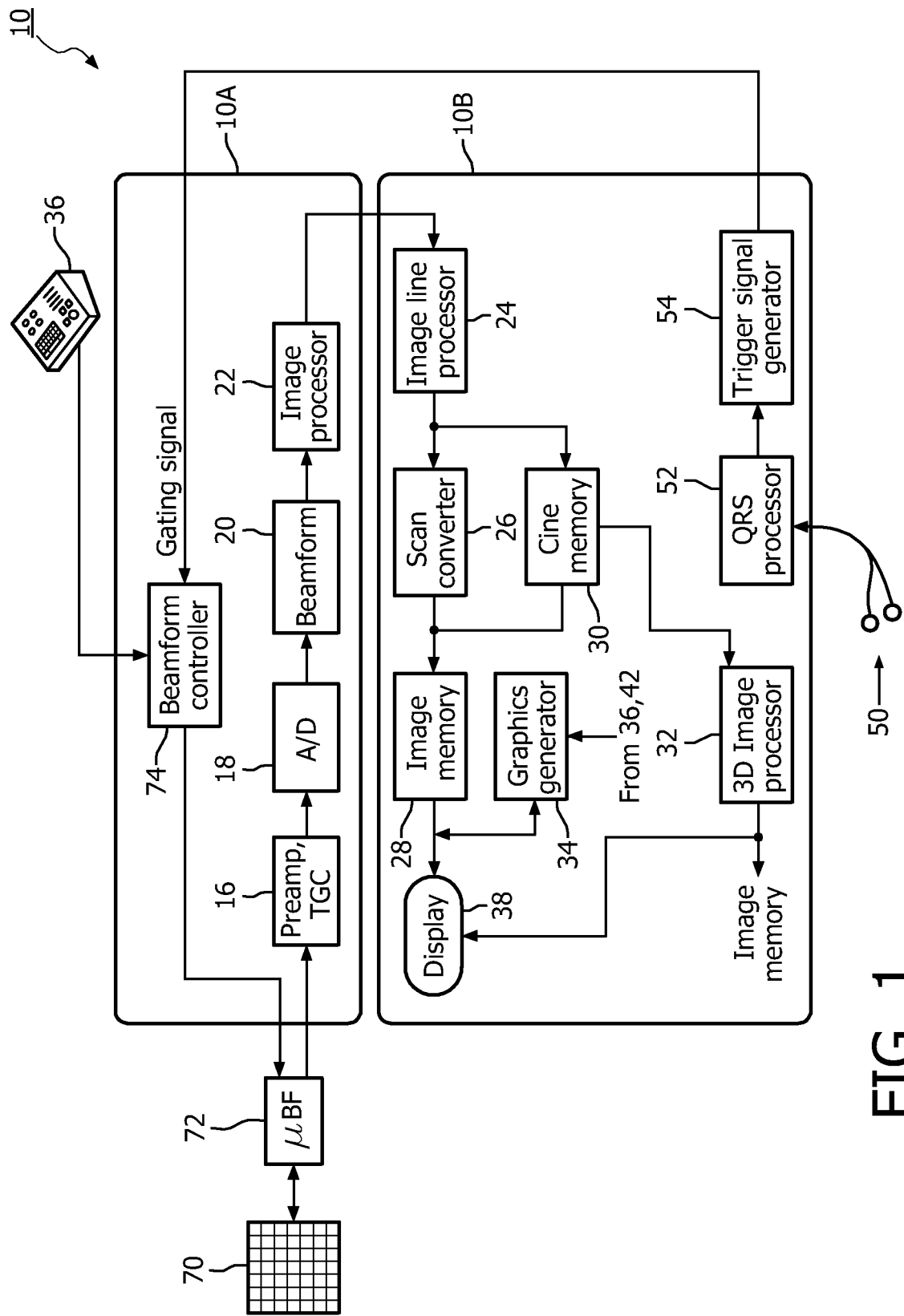
FIG. 1 illustrates in block diagram form an ultrasonic diagnostic imaging system constructed in accordance with the principles of the present invention.

Referring first to FIG. 1, an ultrasound system 10 constructed in accordance with the principles of the present invention is shown in block diagram form. The ultrasound system is configured by two subsystems, a front end acquisition subsystem 10A and a display subsystem 10B. An ultrasound probe is coupled to the acquisition subsystem which includes a two-dimensional matrix array transducer 70 and a micro-beamformer 72. The micro-beamformer contains circuitry which control the signals applied to groups of elements ("patches") of the array transducer 70 and does some processing of the echo signals received by elements of each group. Micro-beamforming in the probe advantageously reduces the number of conductors in the cable between the probe and the ultrasound system and is described in U.S. Pat. No. 5,997,479 (Savord et al.) and in U.S. Pat. No. 6,436,048 (Pesque), and provides electronic steering of beams on transmit and receive for high frame rate real-time (live) imaging.

The probe is coupled to the acquisition subsystem 10A of the ultrasound system. The acquisition subsystem includes a beamform controller 74 which is responsive to a user control 36 and provides control signals to the microbeamformer 72, instructing the probe as to the timing, frequency, direction and focusing of transmit beams. The beamform controller also control the beamforming of echo signals received by the acquisition subsystem by its control of analog-to-digital (A/D) converters 18 and a beamformer 20. Partially beamformed echo signals received by the probe are amplified by preamplifier and TGC (time gain control) circuitry 16 in the acquisition subsystem, then digitized by the A/D converters 18. The digitized echo signals are then formed into fully steered and focused beams by a main system beamformer 20. The echo signals are then processed by an image processor 22 which performs digital filtering, B mode and M mode detection, and Doppler processing, and can also perform other signal processing such as harmonic separation, speckle reduction, and other desired image signal processing.

The echo signals produced by the acquisition subsystem 10A are coupled to the display subsystem 10B, which processes the echo signals for display in the desired image format. The echo signals are processed by an image line processor 24, which is capable of sampling the echo signals, splicing segments of beams into complete line signals, and averaging line signals for signal-to-noise improvement or flow persistence. The image lines for a 2D image are scan converted into the desired image format by a scan converter 26 which performs R-theta conversion as is known in the art. The scan converter can thus format rectilinear or sector image formats. The image is then stored in an image memory 28 from which it can be displayed on a display 38, as described in more detail in FIG. 3. The image in memory is also overlaid with graphics to be displayed with the image, which are generated by a graphics generator 34 which is responsive to the user control 36 so that the graphics produced are associated with the images of the display. Individual images or image sequences can be stored in a cine memory 30 during capture of image loops or sequences.

For real-time volumetric imaging the display subsystem 10B also includes a 3D image rendering processor 32 which receives image lines from the image line processor 24 for the rendering of real-time three dimensional images. The 3D images can be displayed as live (real time) 3D images on the display 38 or coupled to the image memory 28 for storage of the 3D data sets for later review and diagnosis.

An ECG subsystem is provided for use when it is desirable to acquire images at particular phases of the heart cycle. ECG leads 50 provide ECG signals for a QRS processor 52 which identifies the R-wave of each heartbeat. The timing of the R-wave is used to acquire images of a particular heart cycle. Images of the heart at the end diastole phase of a succession of heartbeats can be acquired by coupling the R-wave timing as a trigger signal from a trigger signal generator 54 for the beamform controller 74 and the controls of the control panel 36 used to select the desired heart phase at which heart phase-gated images are to be acquired.

Figure 2:
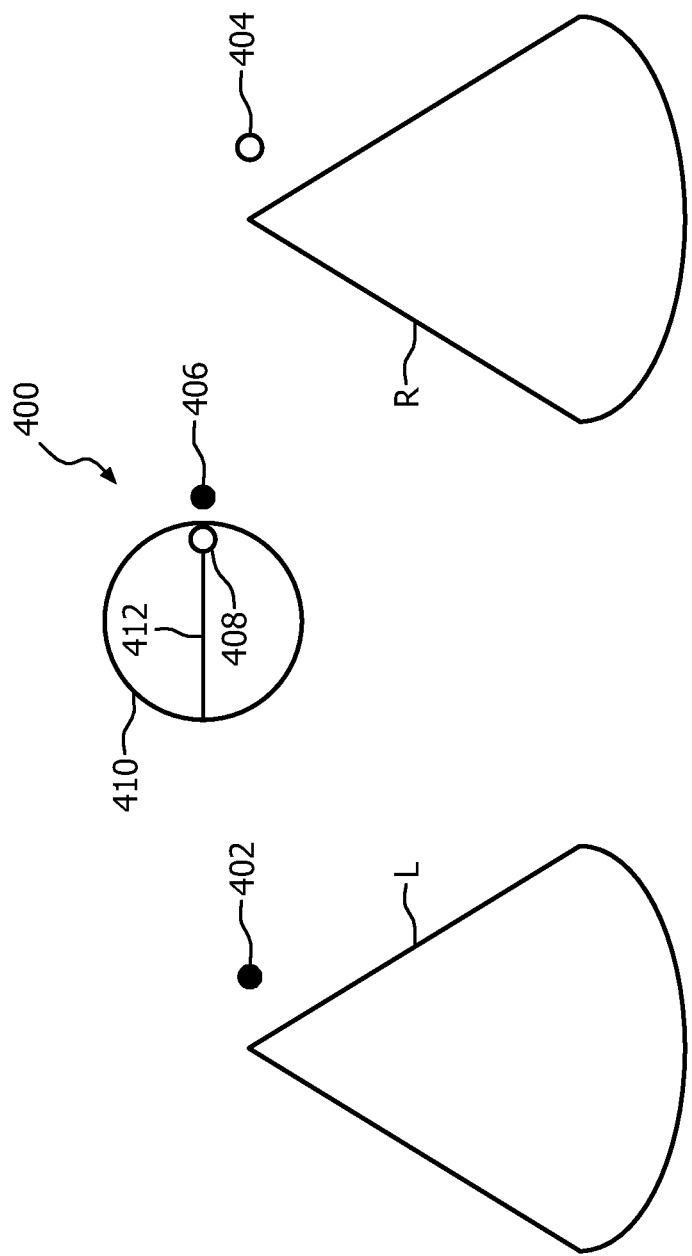
FIG. 2 illustrates a biplane display of the prior art.

When the matrix array probe is operated in the biplane mode, selected by the controls of the control panel 36, the beamform controller 74 is controlled to alternately acquire images of two different image planes in rapid, real-time succession. The controls of the control panel 36 are used to select the desired biplane mode, e.g., the rotate, tilt, or elevation tilt mode. The live images of the two planes are displayed side-by-side as shown in FIG. 2. The sonographer will hold the matrix array probe steady so that the target anatomy is constantly displayed in the reference image, then manipulate a control of the control panel to tilt, rotate, or elevate the second image. As illustrated in the example of FIG. 2, the reference image L is displayed on the left side of the display screen and the adjustable second image R is shown on the right side of the screen. To the right of the apex of each image in FIG. 2 is a probe orientation marker 402, 404 displayed as a dot next to each image. The displayed marker correlates with a mark on the probe which denotes the left or right side of the image, depending on how the sonographer is holding the probe. This marker orients the displayed images in relation to how the sonographer is holding the probe against the body of the patient. Above images L and R in the center of the screen is an image orientation icon 400 which indicates the relative orientation of the two biplane image planes. The icon 400 represents a view of the image planes as seen from the transducer array of the probe and has a circle 410 which graphically represents the space in which the R image can move as it is rotated. The dot 406 corresponds to the dot 402 of the left reference image L and indicates in this example that the plane of the reference image is in a horizontal orientation across the circle 410 with the marker at the right of the image. The line 412 of the icon indicates that the right (movable) image R is in the same orientation with the right marker 408, corresponding to dot 404, at the right side of the image. As the movable image plane is rotated, the line 412 rotates around the circle in correspondence with the plane's changing orientation. Further details of this standard biplane display for the tilt and rotate modes are found in the '394 patent. Details of the biplane display for an elevation tilt mode are found in the '786 patent.

Figure 3:
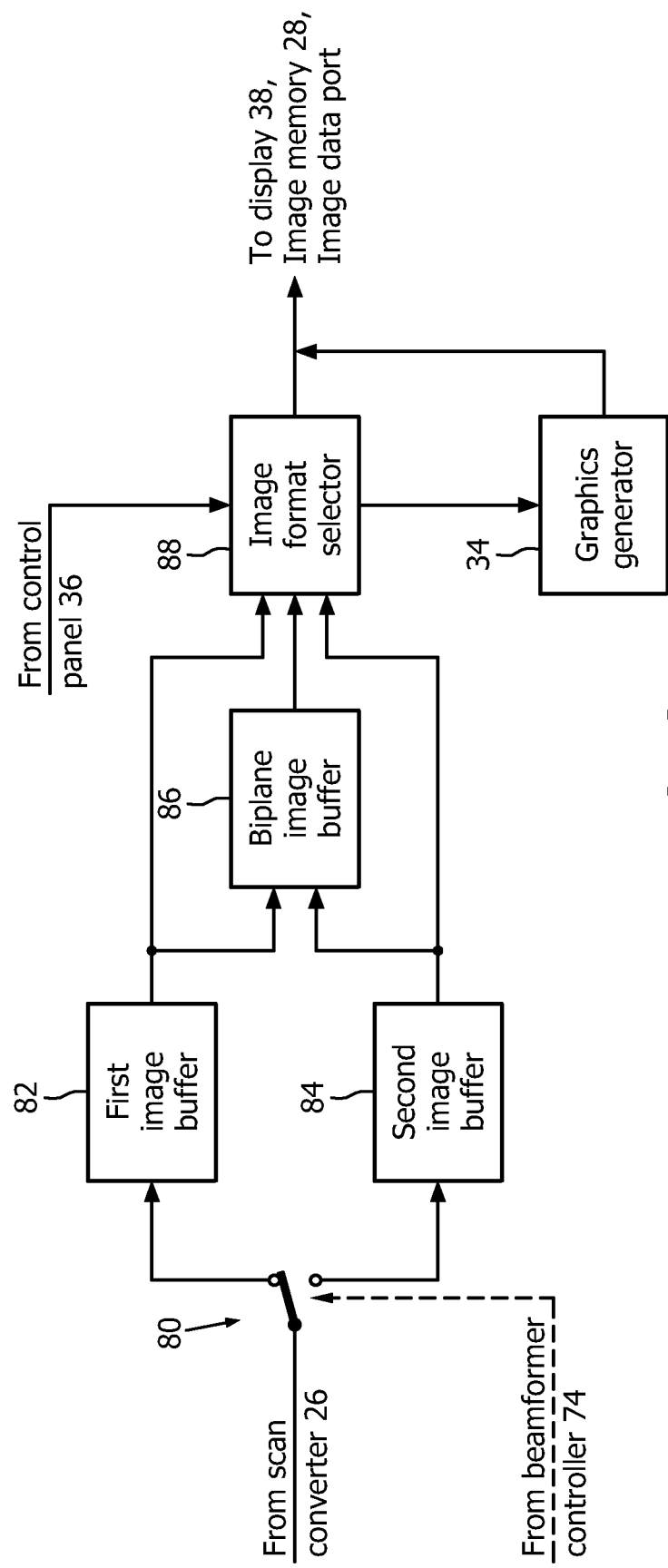
FIG. 3 illustrates in block diagram form the biplane image format selection subsystem of the ultrasound system of FIG. 1

In accordance with the principles of the present invention, the biplane images may be displayed, stored, and/or exported either in the standard format with both images in the same display frame, or as independent images. FIG. 3 illustrates an example of a display processor for the ultrasound system of FIG. 1 which provides this capability. The image display lines from the scan converter 26 are alternately steered by a switch 80 to either a first image buffer 82 or a second image buffer 84. The setting of the switch 80 is controlled by a signal from the beamformer controller 74 in correspondence with the biplane image currently being acquired by the system. Reference biplane images are assembled in the first image buffer 82 and the second (variable orientation) images are assembled in the second image buffer 84. From these two image buffers different storage and display formats can be produced. The image buffers 82 and 84 are coupled to inputs of an image format selector 88. The image buffers 82 and 84 are also coupled to inputs of a biplane image buffer 86, in which both biplane images are formatted for storage and/or display as a single image frame. The output of the biplane image buffer 86 is coupled as a third input of the image format selector 88. The image format selector 88 is then capable of producing as an output, as commanded by a user controlled signal from control panel 36, either image frames of the reference image, image frames of the second (variable orientation) image, or image frames of the standard biplane display of both images simultaneously. The graphics generator 34 is coupled to the selector 88 so as to provide a corresponding graphic overlay for the selected image type. Image frames of the selected format can be displayed on the image display 38, saved in image memory 28, and/or communicated externally through the system's image data port (not shown). This means that a sequence of only variable orientation images can be stored and exported to other storage or display devices, independent of the reference images. It is also possible to store and/or export both a sequence of reference images and an independent sequence of variable orientation images which were acquired at the same time. The two image sequences can be replayed simultaneously for display in synchronism by using the acquisition times of the images stored in the metadata of the image data or with reference to the timing (ECG) signal which dictated the timing of acquisition of both sets of images. It will be appreciated that the acquired images may be static images or live images of flow or motion in the body.

Figure 4:
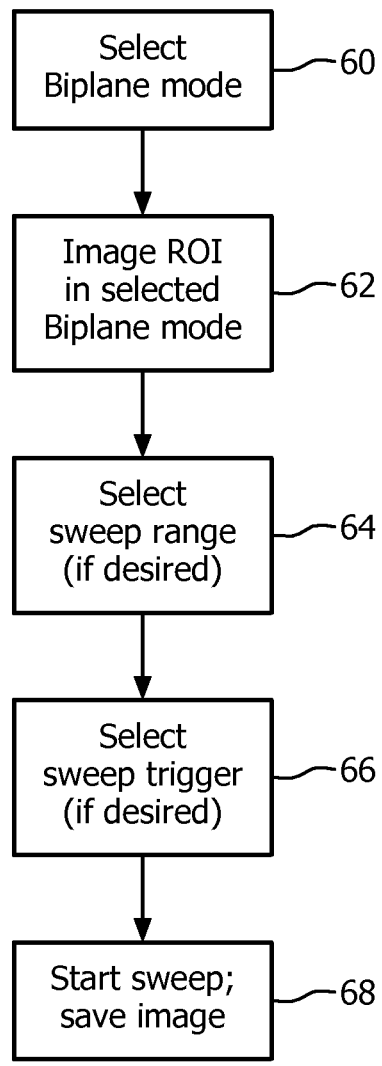
FIG. 4 is a flowchart illustrating the setup and acquisition of biplane sweep images in accordance with the principles of the present invention.

In accordance with a further aspect of the present invention, FIG. 4 illustrates a method of operating the ultrasound system of FIG. 1 to automatically sweep through and acquire a sequence of variable orientation images of the biplane image pair. For example, the reference image may be a sector image with a sector angle ranging from +45° to −45°; the 0° angle of the sector reference image is the central axis of the sector image extending normal from the array transducer. A variable tilt image can then be located anywhere in the range of tilt angles of +45° to −45°. In the biplane imaging systems of the prior art, the tilt orientation of the second image is manually adjustable. The operating sequence of FIG. 4 illustrates how the ultrasound system may be commanded to automatically sweep through the full range or a partial range of second image orientations. For instance, following the above example, the system can be commanded to sweep through and acquire images over the full range of tilt angles from +45° to −45°. Or, images can be acquired over a portion of this full range. The method begins with the step 60 of selecting the desired biplane mode. Examples of biplane modes were given above, including tilt, rotate and elevation tilt modes. Once the mode has been selected, the probe is manipulated in step 62 until an anatomical region of interest is seen in the reference image of the desired biplane mode. For cardiac imaging the region of interest might be the left ventricle of the heart, for example. In step 64 the range through which the orientation is to be swept is selected, if desired. Typically, the full range of orientation will be the default sweep range, e.g., +45° to −45° in this example. In step 66 triggering of the sweep is selected if desired. For instance, it may be desirable to start the sweep as the heart is approaching and continuing through the end diastole phase of the heartbeat. Once the desired parameters for the acquisition have all been set, a button on the control panel 36 is pressed to initiate the sweep, or to activate the trigger to start the sweep at the desired timing. The beamformer controller quickly acquires a sequence of second (orientation variable) images, each at a successively different orientation. At the end of the acquisition the sequence of images is stored for later review or export to another system such as a diagnostic workstation.

In addition to the settings illustrated in FIG. 4, an additional setting can be the angular spacing between successive images. The reader will appreciate that a sweep sequence of closely spaced images will acquire many images but that it will take longer to acquire the greater number of images than a more coarsely spaced sequence.

FIGS. 5a and 5b illustrate two types of biplane images that may be displayed, stored and/or transmitted to another device in accordance with the present invention. FIG. 5a shows a single static image 90 such as a reference image that might be assembled in the first image buffer 82, then displayed on display 38 and stored as a single image. The image 90 can be a single biplane reference image or a single biplane variable orientation image. Instead of a static image, the image 90 can also be a loop or sequence of live images in which the anatomy in the single image is observed moving in real time. FIG. 5b illustrates a sequence of images 92 such as would be acquired by an automated sweep through a range of image plane orientation angles as described above. The sequence in this example is seen to comprise tilt orientations beginning with +45°, then moving in one degree increments so that the second image in the sequence has a tilt orientation of +44°, and so on. In the middle of the sequence is an image with the nominal 0° tilt, and at the end of a sequence swept through a range of +45° to −45° is an image tilted at an orientation of −45° in this example. The swept sequence 92 can be saved and recalled for later review and diagnosis, when the clinician can proceed through the sequence to find an orientation best suited for making a diagnosis. It will further be appreciated that each of the tilted images can be a single static image, a live image loop, and/or gated images which are acquired at a predetermined phase of moving anatomy.

The invention claimed is:

1. An ultrasonic diagnostic imaging system for automated acquisition of a sequence of biplane images of progressively different image plane orientations, the system comprising:
    an ultrasound probe including a two dimensional matrix array transducer;
    a controller which is configured to control the probe to acquire biplane images of different image orientations;
    a user control operable by a user to command the controller to acquire a biplane image pair including a first image in a stationary reference image plane and a second image in a variable orientation image plane, wherein the user control is further operable, after displaying the biplane image pair, to:
        receive user input to change an orientation of the variable orientation image plane of the second displayed image relative to the stationary reference image plane of the first displayed image to select a starting image plane;
        command the controller to acquire a sequence of the biplane image pairs, wherein the variable orientation image plane of the second image is progressively swept through a range of different orientations, starting from the starting image plane, during acquisition of the sequence of the biplane image pairs, and wherein the stationary reference image plane of the first image is unaltered during acquisition of the sequence of biplane image pairs;
        command the controller to selectively discard the first image in the stationary reference image plane of each biplane image pair in the sequence; and
        command the controller to selectively store, independent of the first image, the second image in the variable orientation image plane of each biplane image pair in the sequence; and
    a display for displaying one or more images of the sequence.

2. The ultrasonic diagnostic imaging system of claim 1, further comprising a user control operable to receive user input for setting the range of orientations.

3. The ultrasonic diagnostic imaging system of claim 2, further comprising a source of trigger signals, coupled to the controller, for gated acquisition of a sequence of images of progressively different image orientations.

4. The ultrasonic diagnostic imaging system of claim 1, further comprising an image memory for storing an acquired sequence of images of progressively different image orientations.

5. The ultrasonic diagnostic imaging system of claim 4, wherein the progressively different image orientations are different tilt angle orientations, different rotation angle orientations, or different elevation tilt angle orientations.

6. The ultrasonic diagnostic imaging system of claim 1, further comprising a user control operable by a user for setting the difference in orientation between different image orientations.

7. The ultrasonic diagnostic imaging system of claim 1, further comprising first and second image buffers, and wherein the controller is further configured to direct, in alternating succession during real-time acquisition of image data, display image lines associated with reference images to the first image buffer and display image lines associated with variable orientation images to the second image buffer.

8. The ultrasonic diagnostic imaging system of claim 1, further comprising a user control operable by a user to select a biplane mode as one of: the second image having a tilted orientation in relation to the first image and intersecting the plane of the first image; the second image having a rotated orientation in relation to the first image; or the second image being tilted in elevation and not intersecting the first image.

9. A method for operating an ultrasonic diagnostic imaging system to acquire biplane images comprising:
    selecting a biplane imaging mode, wherein the selecting comprises receiving user input;
    selecting a stationary reference image plane;
    acquiring at least one biplane image including a first image in the stationary reference image plane and a second image in an adjustable image plane;
    changing an orientation of the adjustable image plane of the second image relative to the stationary reference image plane of the first image responsive to the user input after displaying the biplane image to select a starting image plane;
    imaging a region of interest in a body in the selected biplane imaging mode;
    initiating a swept acquisition of a sequence of biplane images of progressively different image orientations, starting from the starting image plane, wherein the sequence of images is acquired by sweeping an imaging plane corresponding to the adjustable image plane through a range of orientations while maintaining an orientation of the stationary reference image plane; and
    from the sequence of biplane images, storing only a sequence of images of progressively different image orientations from the adjustable image plane and discarding a sequence of images in the stationary reference image plane.

10. The method of claim 9, further comprising selecting the range of orientations responsive to user input prior to initiating the swept acquisition.

11. The method of claim 10, further comprising selecting an incremental difference in orientation between different image orientations.

12. The method of claim 9, wherein initiating further comprises initiating a swept acquisition of a sequence of images of progressively different image plane tilt.

13. The method of claim 9, wherein initiating further comprises initiating a swept acquisition of a sequence of images of progressively different image plane rotation.

14. The method of claim 9, further comprising exporting the stored sequence of images to a different image display device.

15. The method of claim 9, further comprising:
    acquiring a trigger signal; and
    wherein initiating further comprises initiating a gated, swept acquisition of a sequence of images of progressively different image orientations.

16. The method of claim 9, wherein the sweep angle range corresponds to a sector angle of a reference sector image in the stationary reference image plane.

* * * * *